United States Patent [19]
Morser et al.

[11] Patent Number: 5,985,562
[45] Date of Patent: Nov. 16, 1999

[54] METHOD OF DETECTING THROMBOTIC DISEASE RISK ASSOCIATED WITH PLASMA CARBOXYPEPTIDASE B POLYMORPHISMS

[75] Inventors: Michael John Morser, San Francisco; Mariko Nagashima, Belmont, both of Calif.

[73] Assignee: Schering Aktiengesellschaft, Berlin, Germany

[21] Appl. No.: 08/869,057

[22] Filed: Jun. 3, 1997

[51] Int. Cl.[6] .............................. C12Q 1/68; C12P 19/34; G01N 33/53
[52] U.S. Cl. ............................... 435/6; 435/7.1; 435/91.2
[58] Field of Search ................................ 435/6, 91.2, 7.1, 435/810

[56] References Cited

U.S. PATENT DOCUMENTS

| | | |
|---|---|---|
| 5,206,161 | 4/1993 | Drayna et al. . |
| 5,364,934 | 11/1994 | Drayna et al. . |
| 5,474,901 | 12/1995 | Drayna et al. . |
| 5,593,674 | 1/1997 | Drayna et al. . |

OTHER PUBLICATIONS

Eaton et al., "Isolation, Molecular Cloning, and Partial Characterization of a Novel Carboxypeptidase B from Human Plasma," *J. Biol Chem.*, (1991) 266(32):21833–21838.

Bajzar et al. "Purification and Characterization of TAFI, a Thrombin–activable Fibrinolysis Inhibitor," *J. Biol. Chem.* (1995) 270(24):14477–14484.

Bajzar et al. "TAFI, or Plasma Procarboxypeptidase B, Couples the Coagulation and Fibrinolytic Cascades through the Thrombin–Thrombomodulin Complex," *J. Biol. Chem.* (1996) 271(28):16603–16608.

Griffin et al. "Anticoagulant Protein C Pathway Defective in Majority of Thrombophilic Patients," *Blood* (1993) 82(7):1989–1993.

Bertina et al. "Mutation in blood coagulation factor V associated with resistance to activated protein C," *Nature*, (1994) 369:64–67.

Redlitz et al. "Inducible Carboxypeptidase Activity: A Role in Clot Lysis in Vivo," *Circulation*, (1996) 93(7):1328–1330.

Redlitz et al. "Plasma Carboxypeptidases as Regulators of the Plasminogen System," *J. Clin. Invest.* (1995) 96:2534–2538.

Toubin et al.(PNAS, vol. 76(9) pp. 4340–4354) (1979).

*Primary Examiner*—Kenneth R. Horlick
*Attorney, Agent, or Firm*—Wendy L. Washtien

[57] ABSTRACT

Polymorphisms within a plasma carboxypeptidase designated plasma carboxypeptidase B (PCPB) have been identified. The relative distribution of these polymorphs in a patient's blood can be used to assess an individual's risk toward thrombotic disease.

15 Claims, 6 Drawing Sheets

Characterization of PCPB polymorphism

```
      10         20         30         40         50         60         70         80
ATGAAGCTTT GCAGCCTTGC AGTCCTTGTA CCCATTGTTC TCTTCTGTGA GCAGCATGTC TTCGCGTTTC AGAGTGGCCA
TACTTCGAAA CGTCGGAACG TCAGGAACAT GGGTAACAAG AGAAGACACT CGTCGTACAG AAGCGCAAAG TCTCACCGGT
      90        100        110        120        130        140        150        160
AGTTCTAGCT GCTCTTCCTA GAACCTCTAG GCAAGTTCAA GTTCTACAGA ATCTTACTAC AACATATGAG ATTGTTCTCT
TCAAGATCGA CGAGAAGGAT CTTGGAGATC CGTTCAAGTT CAAGATGTCT TAGAATGATG TTGTATACTC TAACAAGAGA
     170        180        190        200        210        220        230        240
GGCAGCCGGT AACAGCTGAC CTTATTGTGA AGAAAAAACA AGTCCATTTT TTTGTAAATG CATCTGATGT CGACAATGTG
CCGTCGGCCA TTGTCGACTG GAATAACACT TCTTTTTTGT TCAGGTAAAA AAACATTTAC GTAGACTACA GCTGTTACAC
     250        260        270        280        290        300        310        320
AAAGCCCATT TAAATGTGAG CGGAATTCCA TGCAGTGTCT TGCTGGCAGA CGTGGAAGAT CTTATTCAAC AGCAGATTTC
TTTCGGGTAA ATTTACACTC GCCTTAAGGT ACGTCACAGA ACGACCGTCT GCACCTTCTA GAATAAGTTG TCGTCTAAAG
     330        340        350        360        370        380        390        400
CAACGACACA GTCAGCCCCC GAGCCTCCGC ATCGTACTAT GAACAGTATC ACTCACTAAA TGAAATCTAT TCTTGGATAG
GTTGCTGTGT CAGTCGGGGG CTCGGAGGCG TAGCATGATA CTTGTCATAG TGAGTGATTT ACTTTAGATA AGAACCTATC
     410        420        430        440        450        460        470        480
AATTTATAAC TGAGAGGCAT CCTGATATGC TTACAAAAAT CCACATTGGA TCCTCATTTG AGAAGTACCC ACTCTATGTT
TTAAATATTG ACTCTCCGTA GGACTATACG AATGTTTTTA GGTGTAACCT AGGAGTAAAC TCTTCATGGG TGAGATACAA
     490        500        510        520        530        540        550        560
TTAAAGGTTT CTGGAAAAGA ACAAACAGCC AAAAATGCCA TATGGATTGA CTGTGGAATC CATGCCAGAG AATGGATCTC
AATTTCCAAA GACCTTTTCT TGTTTGTCGG TTTTTACGGT ATACCTAACT GACACCTTAG GTACGGTCTC TTACCTAGAG
     570        580        590        600        610        620        630        640
TCCTGCTTTC TGCTTGTGGT TCATAGGCCA TATAACTCAA TTCTATGGGA TAATAGGGCA ATATACCAAT CTCCTGAGGC
AGGACGAAAG ACGAACACCA AGTATCCGGT ATATTGAGTT AAGATACCCT ATTATCCCGT TATATGGTTA GAGGACTCCG
     650        660        670        680        690        700        710        720
TTGTGGATTT CTATGTTATG CCGGTGGTTA ATGTGGACGG TTATGACTAC TCATGGAAAA AGAATCGAAT GTGGAGAAAG
AACACCTAAA GATACAATAC GGCCACCAAT TACACCTGCC AATACTGATG AGTACCTTTT TCTTAGCTTA CACCTCTTTC
     730        740        750        760        770        780        790        800
AACCGTTCTT TCTATGCGAA CAATCATTGC ATCGGAACAG ACCTGAATAG GAACTTTGCT TCCAAACACT GGTGTGAGGA
TTGGCAAGAA AGATACGCTT GTTAGTAACG TAGCCTTGTC TGGACTTATC CTTGAAACGA AGGTTTGTGA CCACACTCCT
     810        820        830        840        850        860        870        880
AGGTGCATCC AGTTCCTCAT GCTCGGAAAC CTACTGTGGA CTTTATCCTG AGTCAGAACC AGAAGTGAAG GCAGTGGCTA
TCCACGTAGG TCAAGGAGTA CGAGCCTTTG GATGACACCT GAAATAGGAC TCAGTCTTGG TCTTCACTTC CGTCACCGAT
     890        900        910        920        930        940        950        960
GTTTCTTGAG AAGAAATATC AACCAGATTA AAGCATACAT CAGCATGCAT TCATACTCCC AGCATATAGT GTTTCCATAT
CAAAGAACTC TTCTTTATAG TTGGTCTAAT TTCGTATGTA GTCGTACGTA AGTATGAGGG TCGTATATCA CAAAGGTATA
     970        980        990       1000       1010       1020       1030       1040
TCCTATACAC GAAGTAAAAG CAAAGACCAT GAGGAACTGT CTCTAGTAGC CAGTGAAGCA GTTCGTGCTA TTGAGAAAAC
AGGATATGTG CTTCATTTTC GTTTCTGGTA CTCCTTGACA GAGATCATCG GTCACTTCGT CAAGCACGAT AACTCTTTTG
    1050       1060       1070       1080       1090       1100       1110       1120
TAGTAAAAAT ACCAGGTATA CACATGGCCA TGGCTCAGAA ACCTTATACC TAGCTCCTGG AGGTGGGGAC GATTGGATCT
ATCATTTTTA TGGTCCATAT GTGTACCGGT ACCGAGTCTT TGGAATATGG ATCGAGGACC TCCACCCCTG CTAACCTAGA
    1130       1140       1150       1160       1170       1180       1190       1200
ATGATTTGGG CATCAAATAT TCGTTTACAA TTGAACTTCG AGATACGGGC ACATACGGAT TCTTGCTGCC GGAGCGTTAC
TACTAAACCC GTAGTTTATA AGCAAATGTT AACTTGAAGC TCTATGCCCG TGTATGCCTA AGAACGACGG CCTCGCAATG
    1210       1220       1230       1240       1250       1260       1270       1280
ATCAAACCCA CCTGTAGAGA AGCTTTTGCC GCTGTCTCTA AAATAGCTTG GCATGTCATT AGGAATGTTT AA........
TAGTTTGGGT GGACATCTCT TCGAAAACGG CGACAGAGAT TTATCGAAC CGTACAGTAA TCCTTACAAA TT........
```

FIGURE 1

Nucleotide Sequence of PCPB<sub>Thr147</sub>

Amino Acid Sequence of PCPB

```
     -1 +1
MKLCSLAVLVPIVLFCEQHVFA FQSGQVLAALPRTSRQVQVLQNLTTYEIV        30

LWQPVTADLIVKKKQVHFFVNASDVDNVKAHLNVSGIPCSVLLADVEDLI          80

QQQISNDTVSPRASASYYEQYHSLNEIYSWIEFITERHPDMLTKIHIGSS         130
                          147
FEKYPLYVLKVSGKEQTAKNAIWIDCGIHAREWISPAFCLWFIGHITQFY         180
                 A

GIIGQYTNLLRLVDFYVMPVVNVDGYDYSWKKNRMWRKNRSFYANNHCIG         230

TDLNRNFASKHWCEEGASSSSCSETYCGLYPESEPEVKAVASFLRRNINQ         280

IKAYISMHSYSQHIVFPYSYTRSKSKDHEELSLVASEAVRAIEKTSKNTR         330

YTHGHGSETLYLAPGGGDDWIYDLGIKYSFTIELRDTGTYGFLLPERYIK         380

PTCREAFAAVSKIAWHVIRNV                                     401
```

FIGURE 2

Carboxypeptidase B Activity of PCPBAla147
(Hippuryl-Arg Titration)

Carboxypeptidase B Activity of PCPBThr147
(Hippuryl-Arg Titration)

Characterization of PCPB polymorphism

Genotyping of PCPB

METHOD OF DETECTING THROMBOTIC DISEASE RISK ASSOCIATED WITH PLASMA CARBOXYPEPTIDASE B POLYMORPHISMS

FIELD OF THE INVENTION

This invention relates to a carboxypeptidase that binds plasminogen. In particular, it relates to a plasma carboxypeptidase designated plasma carboxypeptidase B (PCPB) and to the use of polymorphism in the gene for this enzyme to diagnose patients at risk for thrombotic disease.

BACKGROUND OF THE INVENTION

The coagulation and fibrinolytic cascades comprise a series of zymogen to enzyme conversions which terminate in the proteolytic enzymes thrombin and plasmin, respectively (Mann et al., *Ann. N.Y. Acad. Sci.* (1991), Vol. 614, pp. 63–75); K. Collen et al., *Blood* (1991), Vol. 78, pp. 3114–3124; Astrup T., *Semin. Thromb. Hemostasis* (1991), Vol. 17, pp. 161–174). These enzymes catalyze the deposition and removal of fibrin. A proper balance between the activities of the two cascades is required both to protect the organism from excessive blood loss upon injury and to maintain blood fluidity within the vascular system. Imbalances are characterized by either bleeding or thrombotic tendencies, the latter of which are manifested as, for example, heart attacks and strokes.

Thrombomodulin is a component of the blood vessel wall which binds thrombin and changes its specificity from fibrinogen to protein C, yielding anticoagulant rather than procoagulant activity (Esmon, C. T., *FASEB J.* (1995), Vol. 9, pp. 946–955). The thrombin-thrombomodulin complex catalyzes cleavage of protein C to activated protein C, which then downregulates the coagulation cascade by proteolytically inactivating the essential cofactors Factor Va and Factor VLLLa (Esmon et al., *Ann. N.Y. Acad. Sci.* (1991), Vol. 614, pp. 30–43). These events are essential in the regulation of the coagulation cascade.

Early studies suggested that activated protein C is not only an anticoagulant but also profibrinolytic, both in vitro and in vivo (Taylor et al., *Thromb. Res.* (1985), Vol. 37, pp. 639–649; de Fouw et al., *Adv. Exp. Med. Biol.*, Vol. 281, pp. 235–243). It was later determined that protein C only appears profibrinolytic because it prevents the thrombin-catalyzed activation of a previously unknown fibrinolysis inhibitor, whose precursor has been isolated from plasma and designated TAFI (thrombin-activatable fibrinolysis inhibitor) or PCPB (plasma carboxypeptidase B). The zymogen precursor is activated by thrombin, plasmin or by a thrombin-thrombomodulin complex to produce an enzyme with carboxypeptidase B activity, which inhibits plasminogen activation and thereby prolongs fibrinolysis (Bajzar et al., *J. Bio. Chem.* (1996), Vol. 270, pp. 14477–14484).

TAFI was discovered independently in three different laboratories. It initially appeared as an unstable carboxypeptidase B-like entity in human serum and was described by Hendricks et al. (*Biochim. Biophys. Acta* (1990), Vol. 1034, pp. 86–92). Then Eaton et al. (*J. Biol. Chem.* (1991), Vol. 266, pp. 21833–21838) cloned the cDNA, deduced the amino acid sequence, described its activation by trypsin, and analyzed its enzymatic properties toward synthetic carboxypeptidase B substrates. They designated the protein PCPB, for plasma carboxypeptidase B (see U.S. Pat. No. 5,206,161). Wang et al. (*J. Biol. Chem.* (1994), Vol. 269, pp. 15937–15944) independently isolated the activated material and named it carboxypeptidase U, where "U" indicates unstable. Nesheim et al (*J. Biol. Chem.* (1995), Vol. 270, pp. 14477–14484) showed that the protein was both activated by thrombin and inhibits fibrinolysis and gave it the name TAFI (thrombin-activatable fibrinolysis inhibitor). Subsequently, Tan and Eaton (*Biochemistry* (1995), Vol. 34, pp. 5811–5816) studied the trypsin activated enzyme and renamed the protein plasma procarboxypeptidase B (pro-pCPB). The co-identity of TAFI and pro-pCPB (or PCPB, as it was initially designated) has been established by their chromatographic behavior on plasminogen Sepharose and the amino acid sequences present at the activation cleavage site.

Thrombophilia can be defined as a tendency toward venous thromboembolic disease in adults under 50 years old in the absence of known risk factors including, among others, malignancy, immobilization, or major surgery. In principle, a tendency toward venous thrombosis could arise from hyperactive coagulation pathways, hypoactive anticoagulant mechanisms, or hypoactive fibrinolysis. Molecular explanations for some thrombophilic patients have come following the discoveries of hereditary thrombophilia associated with deficiencies of the anticoagulant factors antithrombin III (Egeberg, O., *Throm. Diath. Haemorrh.* (1965) Vol. 13, p. 516), protein C (Griffin et al., *J. Clin. Invest.* (1981), Vol. 68, p. 1370), and protein S (Comp et al., *N. Engl. J. Med.* (1984), Vol. 31, p. 1525). More recently, Dahlback et al. (*Proc. Natl. Acad. Sci USA* (1993), Vol. 90, p.1004) have identified the presence of a single point mutation in the Factor V gene, which results in the replacement of an amino acid within the activated protein C cleavage site of the Factor Va molecule. The presence of this mutation has been useful in screening the population to determine those at risk for thromboembolic (thrombotic) disease.

SUMMARY OF THE INVENTION

The present invention arises from the discovery of the presence of two naturally occurring polymorphs of the PCPB protein, which contain different amino acids at position 1.47: $PCPB_{Ala147}$ and $PCPB_{Thr147}$.

Accordingly, the invention is directed to a method for determining the presence of DNA or protein polymorphs of PCPB in human subjects, said method comprising:

obtaining a tissue or blood sample from the subject;

preparing the sample for analysis; and determining the presence of PCPB polymorphs within the sample.

The invention is further directed to a method for determining the presence of the genes coding for the $PCPB_{Ala147}$ and/or $PCPB_{Thr147}$ polymorphs in a human subject, comprising:

obtaining a blood sample from the subject;

Isolating genomic DNA from the blood sample;

amplifying segments of the genomic DNA associated with the PCPB gene using PCR;

separating the products of PCR using gel electrophoresis;

immobilizing the gel-separated products by transfer to a nylon membrane;

contacting the membrane with PCPB-specific probes; and measuring the amount of hybridization of the probes with the membrane-immobilized DNA.

Another aspect of the invention is directed toward a method for determining the risk of thrombotic disease in a human subject, comprising comparing the relative distribution of $PCPB_{Ala147}$ and $PCPB_{Thr147}$ polymorphs within the subject with an at-risk population profile.

A further aspect of the invention is directed toward a kit for identifying human subjects at risk for thrombotic disease, comprising DNA probes useful in measuring polymorphisms within the PCPB gene of the subject and a table useful for comparing the subject's PCPB polymorph profile with an at-risk population profile.

BRIEF DESCRIPTION OF THE DRAWINGS

FIG. 1 is the nucleotide sequence of the human PCPB (PCPB$_{Thr147}$) (SEQ ID NO:1) disclosed in Eaton et al., *J. Biol. Chem.* (1991), Vol. 266, pp. 21833–21838, with the positions of the nucleic acid substitutions (505 and 678) found in the newly isolated polymorph underlined. In the polymorph designated PCPB$_{Ala147}$, the following substitutions have occurred: 505 (A to G) and 678 (C to T).

FIG. 2 provides an amino acid sequence of the PCPB protein (SEQ ID NO:2) produced from the nucleic acid sequence shown in FIG. 1, in which the amino acid at position 147 is Thr. In PCPB$_{Ala147}$, the amino acid at position 147 is Ala.

FIG. 3A provides data for PCPB$_{Ala147}$ and FIG. 3B provides data for PCPB$_{Thr147}$.

DETAILED DESCRIPTION OF THE INVENTION

Definitions

Figure 3A:
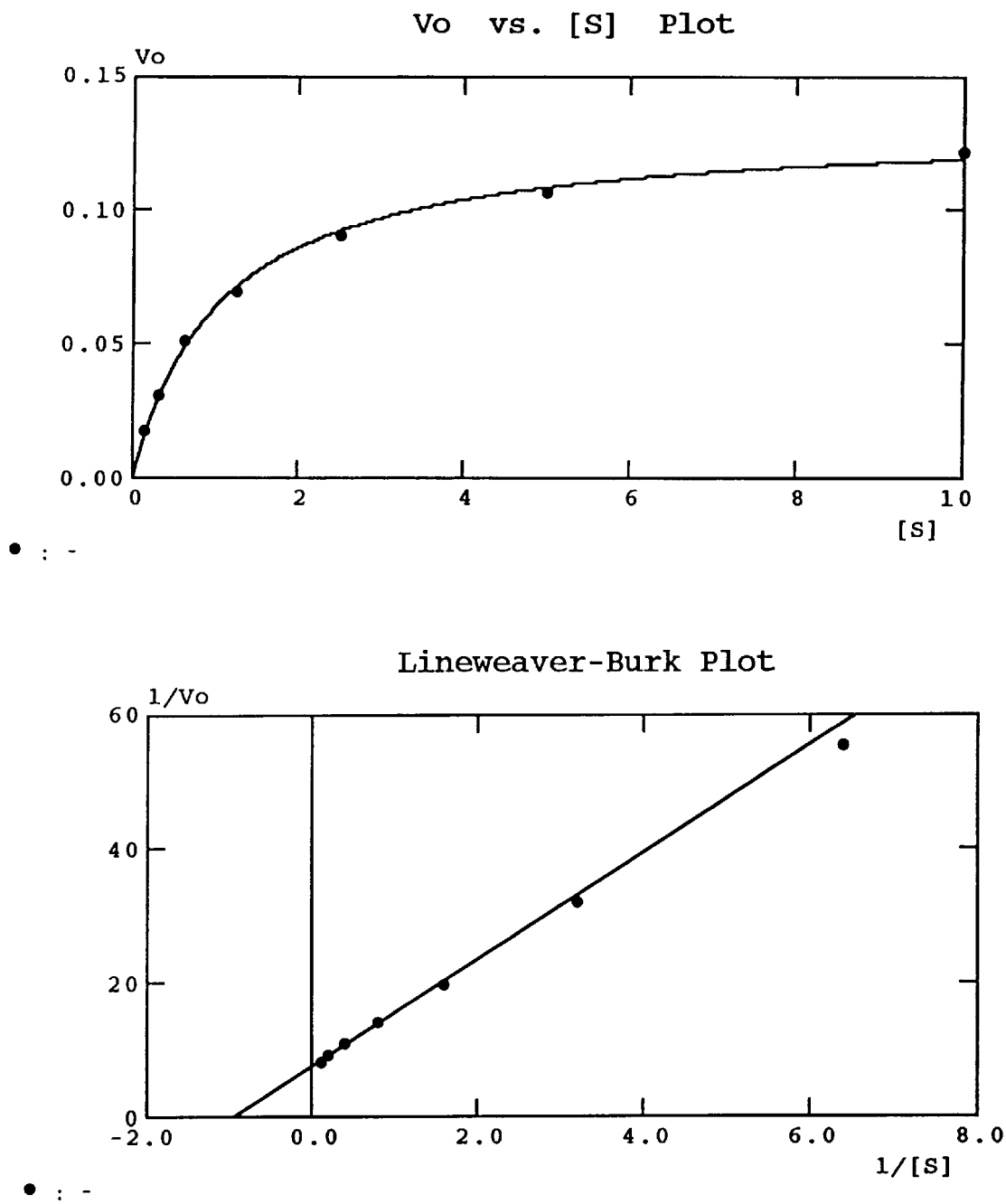
FIGS. 3A and 3B illustrate carboxypeptidase B activity of isolated activated recombinant PCPB$_{Ala147}$ and PCPB$_{Thr147}$.
Figure 3B:
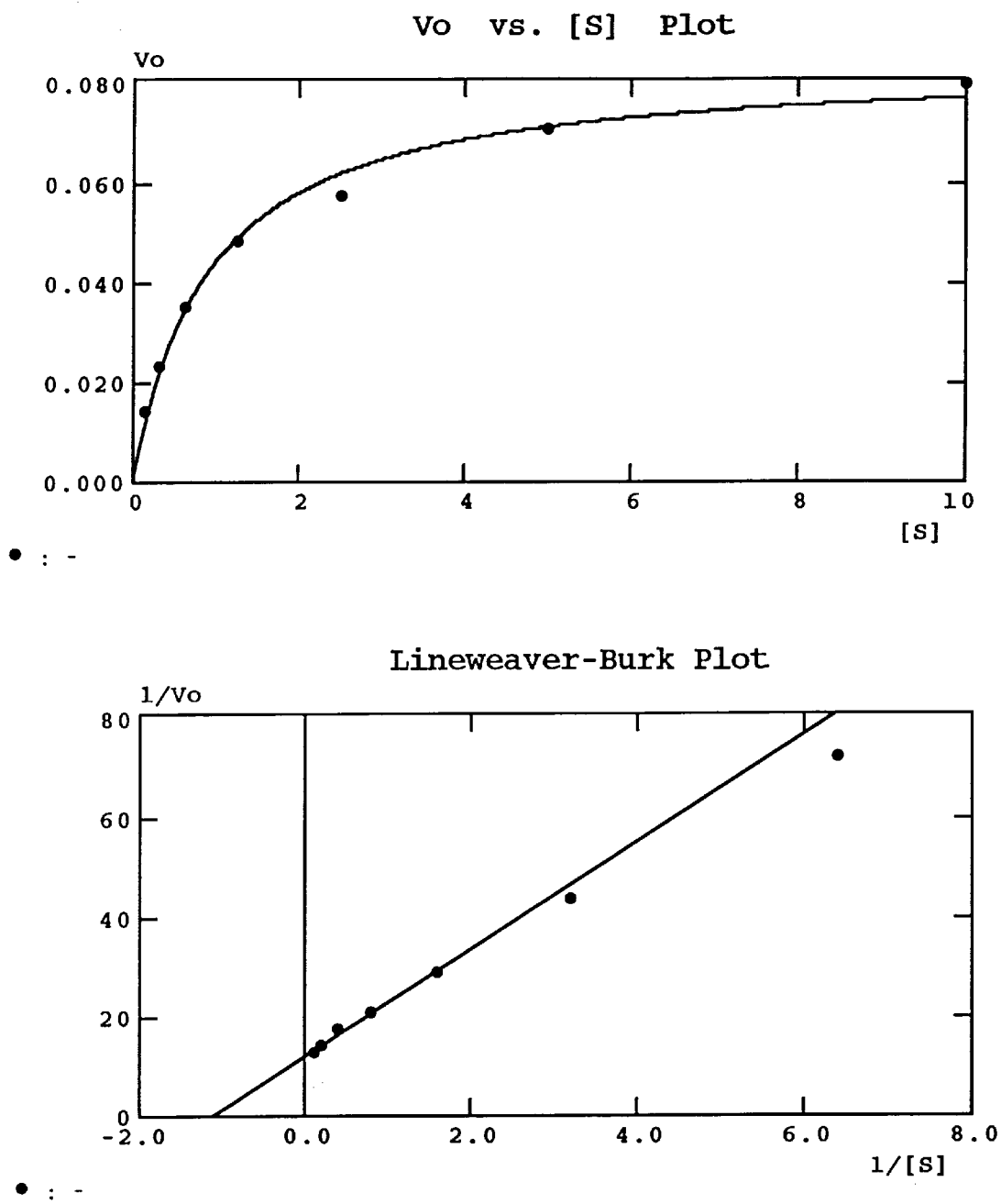

As used in the specification and appended claims, unless specified to the contrary, the following terms have the meaning indicated:

The term "PCPB" refers to the protein described by Eaton et al. (*J. Biol. Chem.* (1991), Vol. 266, pp. 21833–21838 and which has an amino acid sequence substantially homologous to that shown in FIG. 2 (SEQ ID NO:2).

The term "PCPB$_{Thr147}$" refers to an isolated polypeptide whose sequence was published in Eaton et al. (*J. Biol. Chem.* (1991), Vol. 266, pp. 21833–21838) and whose amino acid sequence is shown in FIG. 2 (SEQ ID NO:2).

The term "PCPB$_{Ala147}$" refers to an isolated polypeptide which has an amino acid sequence identical to that of PCPB$_{Thr147}$, except for the substitution of the amino acid Thr by Ala at position 147.

A polypeptide "fragment" or "segment" refers to a stretch of amino acid residues of at least about 6 contiguous amino acids from a particular sequence, more typically at least about 12 amino acids but can be up to 20 amino acids.

A "fragment" or "segment" of a nucleic acid refers to a stretch of at least about 18 nucleotides, more typically at least about 50 to 200 nucleotides but less than 2 kb.

A "polymorphism" refers to a genetically determined heterogeneity of proteins, especially enzymes, and tend to occur when the frequency of a genetic variant in a population is greater than 1%. Frequencies of this order develop by positive selection or by the effect of incidental genetic drift on rare mutations that have a heterozygotic advantage. The resulting polymorphs of a protein differ from each other by substitution or deletion of an amino acid at one or more sites in the peptide chain.

A "polymorph" in the context of a nucleic acid or a gene is an alternative form (allele) of the gene that exists in more than one form in the population. At the polypeptide level, "polymorphs" generally differ from one another by only one, or at most, a few amino acid substitutions.

The term "recombinant" or "recombinant DNA molecule" refers to a polynucleotide sequence which is not naturally occurring, or is made by the artificial combination of two otherwise separated segments of sequence. By "recombinantly produced" is meant artificial combination often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites, regulation sequences, control sequences, or other useful features may be incorporated by design. "Recombinant DNA molecules" include cloning and expression vectors.

The terms "isolated", "substantially pure", and "substantially homogenous", are used interchangably and describe PCPB protein or polypeptide, or fragments thereof, or a DNA segment encoding same, where such protein or peptide, or DNA molecule is separated from components that naturally accompany it. An PCPB polypeptide or fragment thereof, or DNA segment encoding same is substantially free of naturally-associated components when it is separated from the native contaminants which accompany it in its natural state. Thus, a polypeptide that is chemically synthesized or synthesized in a cellular system different from the cell in which it naturally originates will be substantially free from its naturally-associated components. Similarly, a nucleic acid that is chemically synthesized or synthesized in a cellular system different from the cell in which it naturally originated will be substantially free from its naturally-associated components.

The term "homologous", when used to describe a nucleic acid, indicates that two nucleic acids, or designated sequences thereof, when optimally aligned and compared, are identical, with appropriate nucleotide insertions or deletions, in at least 60% of the nucleotides, usually from about 75% to 99%, and more preferably at least about 98 to 99% of the nucleotides.

The term "polymerase chain reaction" or "PCR" refers to a procedure wherein specific pieces of DNA are amplified as described in U.S. Pat. No. 4,683,195, issued Jul. 28, 1987. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. See generally Mullis et al., *Cold Spring Harbor Symp. Quant. Biol.*, 51:263 (1987); Erlich, ed., *PCR Technology*, (Stockton Press, New York, 1989).

The term "residue" refers to an amino acid that is incorporated into a peptide. The amino acid may be a naturally occurring amino acid and, unless otherwise limited, may encompass known analogs of natural amino acids that can function in a similar manner as naturally occurring amino acids. For purposes of this disclosure, amino acid residues are designated herein by their accepted three-letter or one-letter abbreviation, or by the notation "AA", which signifies the presence of an amino acid residue. The amino acids referred to herein are described by shorthand designations as follows:

TABLE 2

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The terms "peptides" and "polypeptides" refer to chains of amino acids whose α carbons are linked through peptide bonds formed by a condensation reaction between the α carbon carboxyl group of one amino acid and the amino group of another amino acid. The terminal amino acid at one end of the chain (amino terminus) therefore has a free amino group, while the terminal amino acid at the other end of the chain (carboxy terminus) has a free carboxyl group.

The term "amino terminus" (abbreviated N-terminus) refers to the free α-amino group on an amino acid at the amino terminal end of a peptide or to the α-amino group (imino group when participating in a peptide bond) of an amino acid at any other location within the peptide. Similarly, the term "carboxy terminus" (C-terminus) refers to the free carboxyl group on the carboxy terminal end of a peptide or the carbonyl group of an amino acid at any other location within the peptide. Typically, amino acids comprising a polypeptide are numbered in order, increasing from the amino terminus to the carboxy terminus of the polypeptide. Thus when one amino acid is said to "follow" another, that amino acid is positioned closer to the carboxy terminal of the polypeptide than the "preceding" amino acid.

The term "immunoglobulin", "antibody" or "antibody peptide(s)" refers to polyclonal antibodies, monoclonal antibodies, to an entire immunoglobulin or antibody or any functional fragment of an immunoglobulin molecule which binds to the target antigen. Examples of such immunoglobulins include complete antibody molecules, antibody fragments, such as Fab, F(ab')2, complementarity determining regions (CDRs), VL (light chain variable region), VH (heavy chain variable region), and any combination of those or any other functional portion of an antibody peptide.

Much of the nomenclature and general laboratory procedures referred to in this application can be found in Sambrook et.al., *Molecular Cloning, A Laboratory Manual* (2nd Ed.), Vol 1–3, Cold Spring Harbor Laboratory, Cold Spring Harbor, N.Y., 1989 or in Berger and Kimmel, *Guide to Molecular Cloning Techniques, Methods in Enzymology* 152 (Academic Press, Inc., San Diego, Calif.). The manuals are hereinafter referred to as "Sambrook" or "Berger" respectively, and are each incorporated herein by reference.

Isolation of PCPB cDNA

DNA encoding PCPB is obtained from a liver cDNA library, or genomic DNA, or by in vitro synthesis. Identification of PCPB DNA most conveniently is accomplished by probing human cDNA or genomic libraries with labelled oligonucleotide sequences selected from the sequence published in Eaton et al. In accord with known criteria, among which is that the sequence should be of sufficient length and sufficiently unambiguous that false positives are minimized. Typically, a $^{32}$P-labelled oligonucleotide having 30 to 50 bases is sufficient, particularly if the oligonucleotide contains one or more codons from methionine or tryptophan. "Isolated" nucleic acid will be nucleic acid that is identified and separated from contaminant nucleic acid encoding other polypeptides from the source of nucleic acid. In the preferred embodiment, PCR was utilized to isolate cDNA clones coding for PCBP polymorphs as described in Examples 1 and 2.

Of particular interest is PCPB nucleic acid that encodes a full-length molecule, including but not necessarily the native signal sequence thereof. Nucleic acid encoding full-length protein is obtained by screening selected cDNA or genomic libraries using the amino acid sequence disclosed in Eaton et al., and, if necessary, using conventional primer extension procedures to secure DNA that is complete at it 5' coding end. Such a clone is readily identified by the presence of a start codon in reading frame with the original sequence.

Cloning of PCPB

A variety of methods for cloning DNA sequences into prokaryotic cells are well known in the art. Organisms which are commonly utilized as hosts for the amplification of a vector include Escherichia, Bacillus and Streptomyces. The most common bacterial hosts are various commercially available strains of *E. coli*, due to the ease with which the organism may be cultured and the wealth of information which is available regarding the cell's life-cycle, genetics, viruses and developmental regulation. The vectors most commonly used in *E. coli* are those derived from the pBR322 plasmid and those derived from lambda or M13 phage, although several vectors unrelated to any of these are also common. The Sambrook and Berger manuals contain methodology sufficient to direct persons of skill through most cloning exercises.

A number of vectors detailed in Sambrook and elsewhere may be initially cloned into *E. coli* and then subsequently transferred into a eukaryotic system without any necessity for re-cloning that part of the vector which is of interest to the person of skill. Vectors capable of replication in both prokaryotic and eukaryotic cells are generally termed "shuttle vectors" and must contain at a minimum a eukaryotic and a prokaryotic origin of replication. Several shuttle vectors are commercially available which contain multi-cloning sites, selectable markers for both bacterial and eukaryotic cells, promoters for both bacterial and eukaryotic expression of the gene(s) of interest, and integration sequences for insertion of the vector into the eukaryotic genome. A few examples of vectors which may be amplified in bacteria and used for transformation in eukaryotic cells include the family of P element vectors for *Drosophila melanogaster*, a number of SV40-derived vectors for the transformation of COS cells, adenovirus-derived vectors for transformation in cells containing the appropriate transcription factor for RNA polymerase III, a variety of BPV-derived vectors and the YIp5-derived vectors of *Sacchromyces cerevosiae* (see Sambrook chapter 16 and Berger chapter 53 for an overview of different vectors which may be transferred between *E. coli* and eukaryotes). General techniques for shuttling DNA between prokaryotes and eukaryotes are also described in Cashion et.al., U.S. Patent No. 5,017,478 and Kriegler, *Gene Transfer and Expression: A Laboratory Manual*, W. H. Freeman, New York, (1990) which are incorporated by reference.

In the preferred embodiment, the mammalian expression vector pcDNA3 and the baculovirus expression vector pBac-PAK8 were used.

Southern blot analysis of genomic DNA and northern blot analysis of RNA using a cloned probe are basic to the art of molecular biology. Sambrook provides adequate guidance to perform most commonly used southern and northern techniques including analysis of genomic DNA, mRNA and cDNA. The present invention provides an array of probes generated from the sequence of any region of the PCPB gene, probes generated from cleavage product of the cloned gene using random-primer or terminal phosphate labeling methods and several other methods known to persons of skill. The probes may be used for a variety of purposes including isolation of homologous genes from other species by screening genomic or expression libraries or performing PCR, identification of PCPB in tissues which express the PCPB gene using in situ or northern analysis, and identification of conditions which influence PCPB expression.

Expression of PCPB

Once the DNA encoding the PCPB protein is isolated and cloned, one may express the ligand in a recombinantly engineered cell such as bacteria, yeast, insect (especially employing baculoviral vectors), and mammalian cells. Methods for expression of recombinant proteins may be found in Sambrook chapters 16 and 17. It is expected that those of skill in the art are knowledgeable in the numerous expression systems available for expression of the DNA encoding PDCPB protein. No attempt to describe in detail the various methods known for the expression of proteins in prokaryotes or eukaryotes will be made.

In brief summary, the expression of natural or synthetic nucleic acids encoding PCPB protein will typically be achieved by operably linking the DNA or cDNA to a promoter (which is either constitutive or inducible), and then incorporating the promoter-DNA construct into an expression vector. The vector should be suitable for replication and integration in either prokaryotes or eukaryotes. Typical expression vectors contain transcription and translation terminators, initiation sequences, and promoters useful for regulation of the expression of the polynucleotide sequence encoding PCPB protein. To obtain high level expression of a cloned gene, such as those polynucleotide sequences encoding PCPB protein, it is desirable to construct expression plasmids which contain, at the minimum, a strong promoter to direct transcription, a ribosome binding site for translational initiation, and a transcription/translation terminator.

a. Expression in Prokaryotes

Methods for the expression of cloned gene in bacteria are well known. Generally, to obtain high level expression of a cloned gene in a prokaryotic system, it is essential to construct expression vectors which contain, at the minimum, a strong promoter and regulator to direct mRNA transcription and termination. Examples of regulatory regions suitable for this purpose are the promoter and operator region of the *E. coli* β-galactosidase gene, the *E. coli* tryptophan biosynthetic pathway, or the leftward promoter from the phage lambda. The inclusion of selection markers in DNA vectors transformed in *E. coli* aid in the isolation of transformed bacteria. Examples of such markers include the genes specifying resistance to ampicillin, tetracycline, or chloramphenicol. In a preferred embodiment, a pUC19-based vector was used for the subcloning and amplification of the desired gene sequences.

The PCPB protein produced by prokaryotic cells may not fold properly. During purification from *E. coli*, the expressed polypeptides may first be denatured and then renatured. This can be accomplished by solubilizing the bacterially produced proteins in a chaotropic agent such as guanidine HCl and reducing all cysteine residues with a reducing agent such as beta-mercaptoethanol. The polypeptides are then renatured, either by slow dialysis or by gel filtration (see U.S. Pat. No. 4,511,500).

b. Expression in Eukaryotes

A variety of eukaryotic expression systems such as yeast, insect cell lines and mammalian cells, are known to those of skill in the art. As explained briefly below, PCPB proteins may also be expressed in these eukaryotic systems.

1. Expression in Yeast

Synthesis of heterologous proteins in yeast is well known and described. *Methods in Yeast Genetics*, Sherman, F., et al., Cold Spring Harbor Laboratory, (1982) is a well recognized work describing the various methods available to produce the AG175 polypeptides in yeast. Examples of promoters for use in yeast include GAL1,IO (Johnson and Davies, *Mol. Cell. Biol.*, 4: 1440–1448 (1984)) ADH2 (Russell et al., *J. Biol. Chem.*, 258: 2674–2682 (1983)), PHO5 (*E.M.B.O.J.*, 6: 675–680, (1982)), and MFal (Herskowitz and Oshima, pp. 181–209 in *The Molecular Biology of the Yeast Saccharomyces*, Strathern et al., eds. Cold Spring Harbor Lab., Cold Spring Harbor, N.Y. (1982)). A multicopy plasmid with a selective marker such as Leu-2, URA-3, Trp-l, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature. See, for example, Botstein, et at, *Gene*, 8:17–24 (1979) and Broach et al., *Gene*, 8:121–133 (1979).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs *Nature*, 275: 104–109 (1978) and Hinnen, et at *Proc. Natl. Acad. Sci. USA*, 75: 1929–1933 (1978). The second procedure does not involve removal of the cell wall. Instead the cells are treated with lithium chloride or acetate and PEG and put on selective plates. Ito et al., *J. Bact.*, 153:163–168 (1983).

The PCPB protein can be isolated from yeast by lysing the cells and applying standard protein isolation techniques to the lysates. The monitoring of the purification process can be accomplished by using Western blot techniques or radioimmunoassays or other standard immunoassay techniques.

2. Expression in Mammalian and Insect Cell Cultures

The DNA sequences encoding PCPB proteins can be ligated to various expression vectors for use in transforming host cell cultures. The vectors preferably contain a marker such as dihydrofolate reductase or metallothionein to provide a phenotypic trait for selection of transformed host cells. Cell cultures useful for the production of the PCPB protein are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, Cos-7 or MDCK cell lines. In preferred embodiments, CHO and BHK cells were used.

As indicated above, the vector, e.g., a plasmid, which is used to transform the host cell, preferably contains DNA sequences to initiate transcription and sequences to control the translation of the DNA sequence encoding the modified ligand. These sequences are referred to as expression control sequences. When the host cell is of insect or mammalian origin illustrative expression control sequences are obtained from the SV-40 promoter (*Science,* 222: 524–527 (1983)), the CMV I. E. promoter (*Proc. Natl. Acad. Sci.,* 81: 659–663 (1984)) or the metallothionein promoter (*Nature,* 296: 39–42 (1982)). The cloning vector containing the expression control sequences is cleaved using restriction enzymes and adjusted in size as necessary or desirable and ligated with polynucleotides coding for the PCPB protein by means well known in the art. In the preferred embodiment, either a mammalian expression vector, pcDNA3, was used with CHO or BHK cell or a baculovirus expression vector, pBacPAK8, was employed with Sf9 cell. A description of expression using the latter system is presented in Example 3.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.,* 45: 773–781 (1983)).

Additionally, gene sequences to control replication in the host cell may be incorporated into the vector such as those found in bovine papilloma virus type-vectors. See, for example, Saveria-Campo, at pp. 2133–238 in *DNA Cloning Vol. II A Practical Approach,* D. M. Glover, ed. IRL Press, Arlington, Va. (1985).

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. See, for example, Kuchler et al., *Biochemical Methods in Cell Culture and Virology,* (1977). The expressed PCPB protein is isolated from cells grown as suspensions or as monolayers. They are recovered by well known mechanical, chemical or enzymatic means.

c. Expression in Recombinant Vaccinia Virus- or Adenovirus-Infected Cells

In addition to use in recombinant expression systems, the DNA encoding PCPB protein can also be used to transform viruses that transfect host cells in vitro or in vivo. These transfected host cells, in turn express the PCPB protein (see section on expression of PCPB proteins in eukaryotic cells, above).

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the polynucleotides encoding the PCPB polypeptides into plasmids so that they are flanked by viral sequences on both sides. The polynucleotides encoding the PCPB polypeptide are then inserted into the virus genome through homologous recombination.

For example, a recombinant adenovirus can be produced by ligating together two plasmids each containing about 50% of the viral sequence and a nucleotide sequence encoding an PCPB polypeptide. Recombinant RNA viruses such as the alpha virus can be made via a cDNA intermediate using methods known in the art. In the case of vaccinia virus (for example, strain WR), the nucleotide sequence encoding PCPB polypeptide can be inserted in the genome by a number of methods including homologous recombination using a transfer vector, pTKgpt-OFIS as described in Kaslow et al., *Science* 252:1310–1313 (1991), which is incorporated herein by reference.

Alternately the DNA encoding PCPB protein may be inserted into another plasmid designed for producing recombinant vaccinia, such as pGS62 (Langford et al., *Mol. Cell. Biol.* 6: 3191–3199 (1986)). This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding PCPB protein and by immunodetection techniques using antibodies specific for the expressed PCPB protein. Virus stocks may be prepared by infecting cells and harvesting virus progeny.

Purification of PCPB Proteins

The PCPB proteins produced by recombinant DNA technology may be purified by standard techniques well known to those of skill in the art. Where the recombinant protein is secreted directly into the media the media is collected directly. Where the protein is retained either in solution within the cell or as an inclusion body, the cell must be lysed to recover the protein. This is typically accomplished by sonification or maceration.

In either case, the protein is then typically isolated from the cellular debris by filtration, centrifugation, or other means known to those of skill in the art, usually by filtration or centrifugation. The protein is then concentrated by adsorption to any suitable resin such as, for example, Q Sepharose or metal chelators, by ammonium sulfate fractionation, polyethylene glycol precipitation, dialysis, or by ultrafiltration. Other means known in the art may be equally suitable.

If the recombinant PCPB protein is expressed as a fusion protein, it may be necessary to digest the fusion protein with an appropriate proteolytic enzyme or use chemical cleavage (i.e. cyanogen bromide) to release the desired PCPB protein.

Purification of PCPB protein may require the additional use of, for example, gel electrophoresis, capillary electrophoresis, reverse phase HPLC, affinity chromatography, ion exchange chromatography, sizing chromatography or other protein purification techniques well known to those of skill in the art. See, for instance, Scopes, *Protein Purification: Principles and Practice,* Springer-Verlag: New York (1982), *Methods in Enzymology,* Vol. 182: *Guide to Protein Purification.* Deutscher, ed. Academic Press, Inc. New York (1990) both of which are incorporated herein by reference.

In the preferred embodiment, recombinant PCPB proteins (PCPB$_{Ala147}$ and PCPB$_{Thr147}$) were each purified from media using S-sepharose chromatography and plasminogen-affinity chromatography as described in Example 4.

Antibody Production

Full length PCPB protein or fragments thereof will be useful for producing antibodies, either polyclonal or monoclonal. A multitude of techniques available to those skilled in the art for production and manipulation of various immunoglobulin molecules can be readily applied to produce antibodies for use in the present invention. Antibodies which bind to PCPB protein may be produced by a variety of means. The production of non-human monoclonal antibodies, e.g., murline, lagomorpha, equine, etc., is well known and may be accomplished by, for example, immunizing the animal with a preparation of isolated PCPB molecules. Techniques for producing antibodies are well known in the literature, see, e.g., Goding, et al., *Monoclonal Antibodies: Principles and Practice* (2nd ed.) Academic Press, New York; Harlow and Lane, *Antibodies: A Laboratory Manual*, Cold Spring Harbor Laboratory, New York (1988); and are exemplfied by U.S. Pat. Nos. 4,381,292, 4,451,570 and 4,618,577, which are each incorporated herein by reference. Antibody production against PCPB is exemplified in U.S. Pat. No. 5,474,901, which is incorporated herein by reference.

The antibodies generated can be used for a number of purposes, e.g., as probes, in immunoassays, in diagnostics or therapeutics, or in basic studies seeking to dissect the portions of the protein responsible for the described properties of PCPB protein or fragments thereof.

Characterization of PCPB Polymorphs

The PCPB polymorphs are characterized in terms of i) their physicochemical properties, ii) in vitro activities and iii) in vivo activities. Studies of physicochemical properties include determination of molecular weight, carbohydrate content/sequence, isoelectric point, amino acid composition, amino acid sequence, and peptide mapping according to the general methods found in Hugli, ed., *Techniques in Protein Chemistry*, Academic Press, Inc. New York (1989) and Deutscher et al., *Methods in Enzymology*, Vol. 182: *Guide to Protein Purification*, Academic Press, Inc., New York (1990)), which are each incorporated herein by reference.

In vitro activities which can be examined are activation kinetics (binding affinity to thrombin and thrombomodulin), kinetics of carboxypeptidase B-like activity, stability in various media, binding affinity to plasminogen, as well as effects on in vitro clot lysis time. Briefly, PCPB polymorphs are activated by a thrombin/thrombomodulin complex, and effects of thrombin and thrombomodulin concentrations, incubation time and incubation temperature on the activation are studied by following carboxypeptidase B-like activity and the presence of the activation fragment by electrophoresis on SDS/PAGE gels.

Carboxypeptidase B-like activity is assayed by measuring the hydrolysis of substrates such as hippuryl-arginine (Folk et al., *J. Biol. Chem.* (1960), Vol. 235, pp. 2272–2277) or furylacryloyl-alanyl-lysine (Plummer and Kimmel, *Anal. Biochem.* (1980), Vol.108, pp. 348–353). The product, hippuric acid, may be converted to a chromogen to improve the sensitivity of the assay (Hendriks et al., *Clinica Chimica Acta* (1986), Vol. 157, pp. 103–108. The effects of PCPB polymorphs on clot lysis time are investigated using a general plate clot lysis assay (for instance, Beebe and Aronson, *Thrombosis Research* (1987), Vol. 47, pp. 123–128; Jones and Meunier, *Thrombosis and Haemostasis* (1990), Vol. 64, pp. 455–463; Bajzar et al., *J. Biol. Chem.* (1996), Vol. 271, pp. 16603–16608). Spontaneous fibrinolysis in whole human plasma may be studied (for example, as described by Wun and Capuano, *J. Biol. Chem.* (1985), Vol. 260, pp. 5061–5066).

Pharmacokinetics and pharmacology of the two polymorphs in vivo can also be examined. General pharmacokinetics such as clearance rate and plasma half-life are determined using techniques described in *Principles of Drug Action*, Goldstein et al., ed., John Wiley and Sons (1973), which is incorporated herein by reference. The pharmacology of $PCPB_{Thr147}$ and $PCPB_{Ala147}$ may be studied by an introduction of the recombinant proteins into experimental animals or by testing activities in human plasma which contains either one or the other polymorph ex viva. Also mice may be created that express one or other PCPB polymorph by the techniques of homologous recombination. These mice can thentested for their bleeding and fibrinolytic phenotype.

Distribution of PCPB Polymorphism in Individuals

The relative distribution of $PCPB_{Thr147}$ and $PCPB_{Ala147}$ polymorphs (DNA or protein) in a particular individual can be determined by identification of the different polymorplis of PCPB found within a human subject, most easily using a blood specimen. One could use any of a variety of techniques which would distinguish the two polymorphs from each other, based on any of the characteristics described above in which the forms were found to differ. Labeled antibodies specific to each protein polymorph can be used to identify the forms within a blood sample. Alternatively, DNA probes specific to the area within the PCPB DNA where the polymorphism occurs can be used to measure the presence of $PCPB_{Thr147}$ and $PCPB_{Ala147}$ within a patient sample and also to compare the relative distribution of the two species. In the preferred embodiment, PCR is used to amplify appropriate segments within genomic DNA isolated from a subject's blood, the amplified DNA is isolated and then identified using probes characteristic of the two polymorphs. This approach is described in Example 6.

Information concerning the relative distribution of PCPB polymorphs within the general population as compared with that found amongst a population known to be at risk for thrombotic disease can be accumulated by performing analysis of polymorph composition, as described above, on a statistically significant number of human subjects chosen at random, as well as in a population of human subjects known to be at risk for thrombotic disease. Accumulation of sufficient data allows establishment of a PCPB polymorph profile for patients at risk of thrombotic disease. With this profile established, one can screen individuals to identify those within the population at risk for thrombotic disease by determining a subject's PCPB polymorph profile and comparing the subject's values to the at-risk population profile. Such identification is useful in helping doctors to alert those individuals with a propensity toward thrombotic disease to the need for them to appropriately monitor their health and perhaps alter their behavior so as to reduce their risk. The following specific preparations and examples are provided as a guide to assist in the practice of the invention, and are not intended as a limitation on the scope of the invention.

EXAMPLE 1

Isolation of cDNA coding for $PCPB_{Ala147}$ Polymorph

Complementary DNA coding for $Ala_{147}$ polymorph of human plasma carboxypeptidase B (PCPB) was isolated from human liver Quick-Clone cDNA (Cat #7113-1, Promega, Madison, Wis.) by the polymerase chain reaction (PCR) method. The two primers used were 5'-GATGAAGCTTTGCAGCCTTGCA-3' (SEQ ID NO:3) and 5'-CATTAAACATTCCTAATGACA-3' (SEQ ID NO:4), based on the sequence published by Eaton et al., *J. Biol. Chem.* (1991), Vol 266, pp. 21833–21838. Liver cDNA (1 ng) was used as a template with Expand™ High Fidelity PCR kit (Cat #1732641, Boehringer Mannheim, Indianapolis, Ind.) according to the manufacturer's specifications. The conditions for the Perkin Elmer Thermocycler consisted of 35 cycles of;

denaturation at 94° C. for 1 minute annealing at 50° C. for 45 seconds elongation at 72° C. for 1 minute.

The 1.3 kb PCR fragment was subcloned into a pCR2.1 vector (Invitrogen, Carlsbad, Calif.) for DNA sequencing. The DNA sequence was performed on both strands of the DNA using the dideoxy chain termination method described by Sanger et al., *Proc. Natl. Acad. Sci. USA*. 74: 5463–5467 (1977). The DNA sequence is shown in FIG. 1. The DNA sequence isolated differed from the published sequence at two nucleotide positions, one at base 505 (A to G), which resulted in the substitution of threonine at residue 147 with alanine, and the other change at base 678 (C to T), which led to a silent mutation.

EXAMPLE 2

Isolation of cDNA Coding for $PCPB_{Thr147}$ Polymorph

Complementary DNA coding for $Thr_{147}$ polymorph of human PCPB was isolated from total HepG 2 RNA by reverse transcriptase (RT)-PCR method. One µg of total HepG 2 RNA (from Dr. Q. Wu, Berlex Biosciences, Richmond, Calif.) was reverse transcribed using 40 unit of avian myeloblastosis virus reverse transcriptase (Boehringer Mannheim, Indianapolis, Ind.) in a 20 ul reaction mixture containing 50 mM Tris-HCl, 8 mM $MgCl_2$, 30 mM KCl, 1 mM dithiothreitol, pH 8.5, 0.2 µg of oligo (dT) primers, 5 mM each of dATP, dCTP, dTTP and dGTP, 20 unit of RNasin (Boehringer Mannheim) at 42° C. for 60 minutes. Following the heat inactivation at 65° C. for 10 minutes, 1 µl sample of HepG 2 cDNA was used as template in the PCR under the same conditions as described above. The PCR product was subcloned into the pCR2.1 vector, and the clone containing PCPB cDNA coding for Thr147 polymorph was identified by DNA sequencing.

EXAMPLE 3

Baculovirus Expression of Human $PCPB_{Ala147}$ and $PCPB_{Thr147}$

The XHO1/KPN1 fragment of pCR2.1 vectors containing either $PCPB_{Ala147}$ or $PCPE_{Thr147}$ cDNA was subcloned into a pBacPAK 8 vector (Clontech, Palo Alto, Calif.) at XHO1/KPN1 sites in order to place the gene of interests under the control of the AcMNPV polyhedrin promoter. Baculovirus expression of recombinant PCPB polymorphs was performed by co-transfecting the plasmid pBacPAK8/PCPB with a linearized BacPAK6 viral cDNA (Clontech) into *Spodoptera frugiperda* (Sf9) cells according to the manufacturer's instructions. Recombinant plaques were identified and purified by their β-galactosidase negative phenotype. Expression of PCPB protein was confirmed by Western blotting of the media harvested 3 days post infection, with monoclonal antibodies to PCPB purified from plasma (donated by Dr. L. Bajzar, Queen's University, Kingston, Ontario, Canada). Sf9 cells expressing either $PCPB_{Ala147}$ or $PCPB_{Thr147}$ were grown as follows: Non-infected Sf9 cells were grown in shake flasks at 28° C., to a density of $1-1.2\times10^6$ per ml in TNMF (Grace's with supplements from Sigma, St. Louis, Mo.) plus 10% FBS and 0.1% pluronic F-68 (Sigma), and a viability of >97%. One liter of cells was infected with viral stock at MOI of around 0.01. Cultures were harvested between 48 and 72 h post-infection by centrifuging the media at 1200 rpm for 10 minutes. The media was then used for purification of both recombinant PCPB proteins.

EXAMPLE 4

Purification of Recombinant PCPB Proteins

The conditioned media from Sf9 cells containing either recombinant $PCPB_{Ala147}$ or $PCPB_{Thr147}$ proteins were diluted 20-fold with $QH_2O$, the pH adjusted to 6.8, and millipore-filtered prior to S-Sepharose chromatography. A S-Sepharose column (Pharmacia Biotech Inc., Piscataway, N.J.) was equilibrated with an equilibration buffer (20 mM phosphate buffer, pH 6.8). After applying the sample, the column was washed extensively with the equilibration buffer. Bound proteins were eluted from the column with a salt gradient of 0 to 0.5 M NaCl in the equilibration buffer. Ten-ml fractions were analyzed by SDS/PAGE electroporesis of denatured samples, followed by Western blotting using monoclonal antibodies to PCPB. Fractions containing recombinant PCPB were pooled and applied directly onto a plasminogen-affinity column. The plasminogen-affinity column had been prepared as follows; fourty one mg of plasminogen was purified from 650 ml of human plasma on a Lysine-Sepharose column (Pharmacia) according to the manufacturer's instructions. Plasminogen was dialysed against 0.1 M sodium citrate, pH 6.5, and was coupled at 4° C. overnight to 1.5 g of CNBr-activated Sepharose 4B (Pharmacia) that had been washed with 1 mM HCl just prior to use. The remaining active sites on the resin were blocked with 0.1 M Tris buffer, pH 8.0. The resin was washed three times alternatively with 0.1 M acetate buffer/0.5 M NaCl, pH 4.0 and 0.1 M Tris-HCl/0.5 M NaCl, pH 8.0, and finally equlibrated with phosphate-buffered saline (PBS) containing 1 µM D-Val-Phe-Lys chloromethyl ketone (VFL-CMK from Calbiochem-Novabiochem International, San Diego, Calif.). After applying samples, the column was washed extensively with PBS plus 1 µM VFL-CMK. Bound contaminants were eluted from the column with 5 mM epsilon-amino caproic acid (ACA) in PBS. Recombinant PCPB was eluted with 200 mM epsilon ACA in PBS. Four ml fractions were collected into tubes, each containing 8 ml of 0.015% Tween 80 in PBS. Fractions containing recombinant PCPB were identified using silver-staining after SDS/PAGE gel electrophoresis, pooled, and applied onto a small S-Sepharose column to remove epsilon ACA and to concentrate the sample, using essentially the same conditions as for the first column. The purity of the sample was determined by SDS/PAGE gel electrophoresis. The molecular weight of the two polymorphs of recombinant PCFPB isolated in this manner were estimated to be around 50 k-dalton.

EXAMPLE 5

Activation and carboxypeptidase B Activity Assay of PCPB Polymorphs

Recombinant PCPB (0.2 µM) was activated with 10 nM of thrombin (Sigma) and 50 nM of thrombomodulin (Solulin, Berlex Biosciences, Richmond, Calif.) in the activation buffer consisting of 20 mM HEPES, 0.15 M NaCl, 5.0 mM $CaCl_2$, pH 7.4, at room temperature for 10 minutes. Activation was stopped by an addition of 0.34 unit/ml hirudin (Sigma). Activation of recombinant PCPB was confirmed by the decrease in 50 K-dalton band and the appearance of 35 k-dalton fragment in SDS/PAGE gelelectrophoresis. Carboxypeptidase B-like activity of activated recombinant PCPB was measured by the hydrolysis of hippuryl-arginine (Sigma) to hippuric acid. In order to improve the sensitivity of assay, hippuric acid produced was converted to a chromogen with cyanuric chloride dissolved in dioxane, and absorbance of the chromogen was measured at 382 nm, according to the protocol described by Hendriks et al. in Clinica Chimica Acta: 157, 103–108 (1986). The assay has been adapted to a 96-well plate format as follows;

In a 96-well plate, add

24 μl HEPES (50 mM, pH 7.8)

12 μl $QH_2O$

12 μl activated PCPB (dilute 1:1 with the activation beffer)

12 μl hippuryl-Arg (10 mM in 20 mM NaOH)

Incubate at room temperature for 30 to 60 minutes.

To each well, add

80 μl phosphate buffer (0.2 M, pH 8.3)

60 μl cyanuric chloride (Sigma) in dioxane (3%, w/v)

Mix well by pipetting several times and transfer clear supernatants to new wells, and read the absorbance at 382 nm (endpoint).

Include hippuric acid standard (starting with 2.5 mM stock solution, two-fold serial dilution in 20 mM NaOH).

24 μl HEPES (50 mM, pH 7.8)

12 μl $QH_2O$

12 μl the activation buffer

12 μl hippuric acid standards

EXAMPLE 6

Identification of PCPB Polymorphism at Residue 147 in Blood Specimens

Figure 4A:
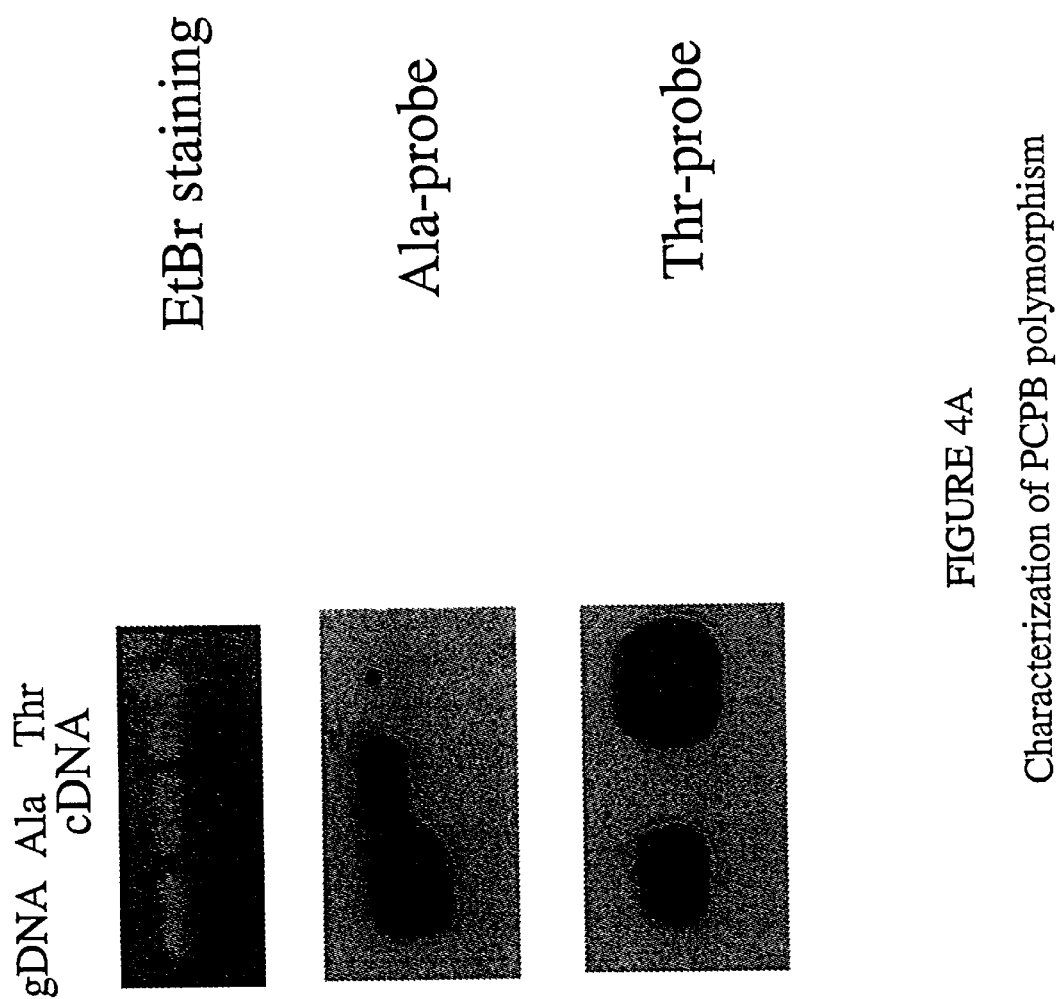
FIG. 4A shows Southern blot analysis of DNA from plasmids containing either PCPB$_{Thr147}$ or PCPB$_{Ala147}$ cDNA, using DNA probes specific for each polymorph.
Figure 4B:
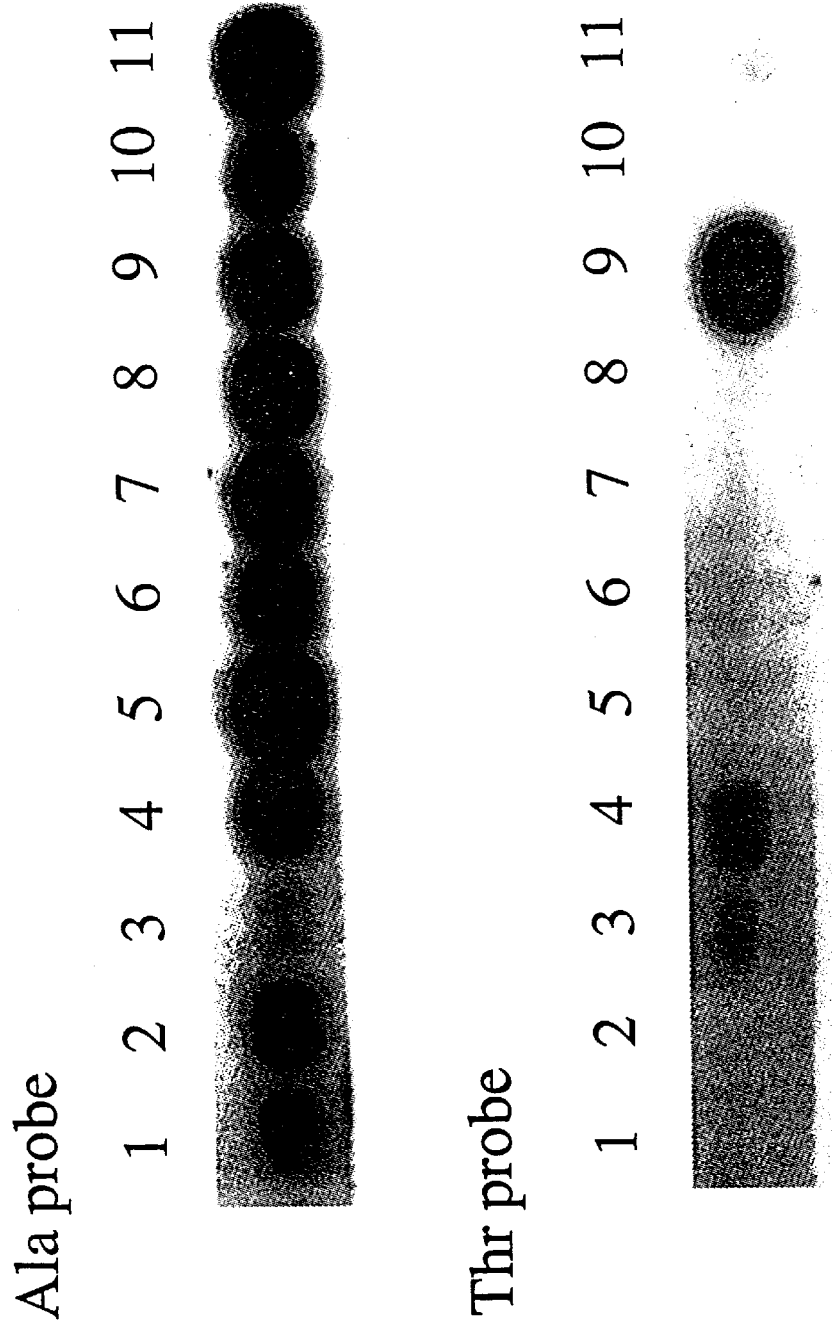
FIG. 4B shows Southern blot analysis of amplified genomic DNA isolated from 11 human blood specimens, using the same probes.

In order to investigate the presence of polymorphism at residue 147 of PCPB in human subjects, PCPB DNA fragments were isolated from genomic DNA using the PCR method. Genomic DNAs were isolated from 200 μl of whole blood from various individuals using QlAamp Tissue Kit (QIAGEN Inc., Santa Clarita, Calif.). Up to 500 ng of genomic DNA was used as a template in the reaction mixture containing 50 mM KCl, 10 mM Tris-HCl, pH 8.3, 1.5 mM MgCl2, 0.2 mM each of dATP, dGTP, dCTP and dTTP, 50 pmole each of primers 5'-ATGGCCTATGAACCACAAG-3' (SEQ ID NO:3) and 5'-GTTTCTGGAAAAGAACAA-3' (SEQ ID NO:4). The conditions for the Perkin Elmer Thermocycler consisted 30 cycles of:

denaturation at 94° C. for 1 minute annealing at 55° C. for 45 seconds elongation at 72° C. for 1 minute Two plasmid DNAs, one coding for the $PCPB_{Ala147}$ polymorph and the other coding for the $PCPB_{Thr147}$ polymorph, were included as internal controls. The 105-base-long PCR products were run in 1.8% agarose gel electrophoresis and transferred to a nylon membrane (Boehringer Mannheim) using 0.5 M NaOH/1.5 M NaCl. Two duplicate membranes were prepared, briefly washed in 2×SSC (30 mM sodium citrate, pH 7.5, 0.3 M NaCl), UV cross-linked, and pre-hybridized in 5×SSC, 1% blocking reagent (Boehringer Mannheim), 0.1% laurylsarcosine, and 0.02% SDS for 20 minutes at 37° C. The membranes were hybridized overnight at 37° C. in the pre-hybridization buffer containing digoxigenin (DIG)-labeled probes. Two oligonucletides, 5'-AAAGAAGCAGCCAAAA-3' (SEQ ID NO:5) (corresponding to the sequence of $PCPB_{Ala147}$) and 5'-AAAGAACAAACAGCCAAAA-3' (SEQ ID NO:6) (corresponding to the sequence of $PCPB_{Thr147}$), were labeled with DIG-11-ddUTP using terminal transferase (Genius 5 Oligonucleotide 3'-End Labeling kit from Boehringer Mannheim). The membranes were washed twice in 2×SSC/0.1% SDS at room temperature, followed by tetramethylammonium chloride (TMA(C) wash solution, consisting of 3.0 M TMAC (Sigma), 50 mM Tris-HCl, pH 8.0, 0.1% SDS and 2 mM EDTA. The membrane hybridized with the DIG-Ala probe was washed twice, 30 minutes each, at 53° C., while the membrane hybridized with the DIG-Thr probe was washed at 50° C. DIG-labeled DNA fragments were detected using alkaline phosphatase conjugated anti-DIG antibodies and chemiluminescent substrate CSPD® (DlG/Genius™ 7 Luminescent Detection kit from Boehringer Mannheim). See FIG. 4.

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for determining the presence of DNA or protein polymorphs of plasma carboxypeptidase B (PCPB) in a human subject, comprising:
    obtaining a tissue or blood sample from the subject;
    preparing the sample for analysis by isolating DNA or protein from the sample; and
    determining the presence of PCPB polymorphs within the sample by analyzing the isolated DNA or protein using probes specific for individual DNA or protein polymorphs of PCPB.

2. The method of claim 1, wherein a blood sample is used.

3. The method of claim 1, wherein the isolated DNA is further prepared for analysis by amplification of the region of the DNA which codes for amino acid position 147 of the protein polymorphs of PCPB.

4. The method of claim 3, wherein the presence of amplified DNA coding for $PCPB_{Ala147}$ and/or $PCPB_{Thr147}$ within the prepared sample is determined using DNA probes wherein the DNA probes hybridize specifically to DNA coding for either PCPBA$_{Ala147}$ or PCPB$_{Thr147}$.

5. The method of claim 4, wherein DNA probes have the sequences 5'-AAAGAACAAGCAGCCAAAA-3' (SEQ ID NO:5) and 5'-AAAGAACAAACAGCCAAAA-3' (SEQ ID NO:6).

6. A method for determining the presence of DNA coding for plasma carboxypeptidase B (PCPB) protein polymorphs, PCPB$_{Thr147}$ and/or PCPB$_{Ala147}$, in a human subject, comprising obtaining a tissue or blood sample from the subject;

isolating DNA from the sample;

amplifying the region of the isolated DNA which codes for amino acid position 147 of the protein polymorphs of PCPB;

separating the amplified DNA using gel electrophoresis;

immobilizing the gel-separated DNA by transfering the DNA to a nylon membrane;

contacting the membrane with DNA probes wherein the DNA probes hybridize specifically to DNA coding for either PCPB$_{Ala147}$ or PCPB$_{Thr147}$; and measuring the amount of hybridization of the probes with the membrane-immobilized DNA.

7. The method of claim 6, wherein hybridization is performed using DNA probes having the sequences 5'-AAAGAACAAGCAGCCAAAA-3' (SEQ ID NO:5) and 5'-AAAGAACAAACAGCCAAAA-3' (SEQ ID NO:6).

8. A test kit for identifying a human subject at risk for thrombotic disease, comprising DNA probes which identify polymorphisms within the plasma carboxypeptidase B (PCPB) gene of the subject and a table containing a profile of the PCPB polymorphism content within a population at risk for thrombotic disease, for comparing the subject's PCPB polymorph profile with that of an at-risk population.

9. A method for determining the presence of plasma carboxypeptidase B (PCPB) protein polymorphs, PCPB$_{Thr147}$ and/or PCPB$_{Ala147}$, in a human subject, comprising obtaining a tissue or blood sample from the subject;

isolating protein material from the sample;

separating the proteins using gel electrophoresis;

immobilizing the gel-separated proteins by transfering the proteins to a nylon membrane;

contacting the membrane with an antibody specific for either PCPB$_{Thr147}$ or PCPB$_{Ala147}$; and measuring the amount of the antibody which is bound to the membrane-immobilized proteins.

10. The method of claim 9, wherein the antibodies are monoclonal.

11. A method for determining the risk of thrombotic disease in a human subject, comprising determining the distribution of plasma carboxypeptidase B (PCPB) polymorphs within a general population and within a population known to be at risk for thrombotic disease and establishing a profile of PCPB polymorphism content for the at-risk population;

obtaining a tissue or blood sample from the subject;

determining the distribution of PCPB polymorphs within the sample by DNA or protein analysis to obtain a profile of PCPB polymorphism content for the subject; and comparing the subject's profile of PCPB polymorphism content with the profile of PCPB polymorphism content determinined for the at-risk population.

12. The method of claim 11 wherein the DNA analysis to obtain the profile of PCPB polymorphism content for the subject comprises:

isolating DNA from the sample;

amplifying the region of the DNA which codes for amino acid position 147 of the PCPB polymorph;

separating the amplified DNA using gel electrophoresis;

immobilizing the gel-separated DNA by transfering the DNA to a nylon membrane;

contacting the membrane with DNA probes wherein the DNA probes hybridize specifically to DNA coding for either PCPB$_{Ala147}$ or PCPB$_{Thr147}$; and measuring the amount of hybridization of the probes with the membrane-immobilized DNA to obtain a profile of PCPB polymorphism content for the subject.

13. The method of claim 12, wherein hybridization is preformed using DNA probed having sequences 5'-AAAGAACAAGCAGCCAAAA-3' (SEQ ID NO:5) and 5'-AAAGAACAAACAGCCAAAA-3' (SEQ ID NO:6).

14. A method for determining the presence of plasma carboxypeptidase B (PCPB) protein polymorphs, PCPB$_{Thr147}$ and/or PCPB$_{Ala147}$, in a human subject, comprising obtaining a tissue or blood sample from the subject;

contacting the sample with an antibody specific for either PCPB$_{Thr147}$ or PCPB$_{Ala147}$; and measuring the amount of the antibody which is bound to the sample.

15. A test kit for identifying a human subject at risk for thrombotic disease, comprising antibodies which specifically identify individual protein polymorphisms of plasma carboxypeptidase B (PCPB) and a table containing a profile of the PCPB polymorphism content within a population at risk for thrombotic disease, for comparing the subject's PCPB polymorph values with those of an at-risk population.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1272 base pairs
      (B) TYPE: nucleic acid
      (C) STRANDEDNESS: double
      (D) TOPOLOGY: linear (ii) MOLECULE TYPE: cDNA (x) PUBLICATION INFORMATION:
            (A) AUTHORS: Eaton, Dan L.
                 Malloy, Beth E.
                 Tsai, Siao P
                 Henzel, William
                 Drayna, Dennis
            (B) TITLE: Isolation, Molecular Cloning, and Partial
                 Characterization of a Novel Carboxypeptidase B
                 from Human Plasma
            (C) JOURNAL: J. Biol. Chem.
            (D) VOLUME: 266
            (E) ISSUE: 32
            (F) PAGES: 21833-21838
            (G) DATE: Nov 15-1991

(xi) SEQUENCE DESCRIPTION: SEQ ID NO:1:

ATGAAGCTTT GCAGCCTTGC AGTCCTTGTA CCCATTGTTC TCTTCTGTGA GCAGCATGTC      60

TTCGCGTTTC AGAGTGGCCA AGTTCTAGCT GCTCTTCCTA GAACCTCTAG GCAAGTTCAA     120

GTTCTACAGA ATCTTACTAC AACATATGAG ATTGTTCTCT GGCAGCCGGT AACAGCTGAC     180

CTTATTGTGA AGAAAAAACA AGTCCATTTT TTTGTAAATG CATCTGATGT CGACAATGTG     240

AAAGCCCATT TAAATGTGAG CGGAATTCCA TGCAGTGTCT TGCTGGCAGA CGTGGAAGAT     300

CTTATTCAAC AGCAGATTTC CAACGACACA GTCAGCCCCC GAGCCTCCGC ATCGTACTAT     360

GAACAGTATC ACTCACTAAA TGAAATCTAT TCTTGGATAG AATTTATAAC TGAGAGGCAT     420

CCTGATATGC TTACAAAAAT CCACATTGGA TCCTCATTTG AGAAGTACCC ACTCTATGTT     480

TTAAAGGTTT CTGGAAAAGA ACAAACAGCC AAAAATGCCA TATGGATTGA CTGTGGAATC     540

CATGCCAGAG AATGGATCTC TCCTGCTTTC TGCTTGTGGT TCATAGGCCA TATAACTCAA     600

TTCTATGGGA TAATAGGGCA ATATACCAAT CTCCTGAGGC TTGTGGATTT CTATGTTATG     660

CCGGTGGTTA ATGTGGACGG TTATGACTAC TCATGGAAAA AGAATCGAAT GTGGAGAAAG     720

AACCGTTCTT TCTATGCGAA CAATCATTGC ATCGGAACAG ACCTGAATAG GAACTTTGCT     780

TCCAAACACT GGTGTGAGGA AGGTGCATCC AGTTCCTCAT GCTCGGAAAC CTACTGTGGA     840

CTTTATCCTG AGTCAGAACC AGAAGTGAAG GCAGTGGCTA GTTTCTTGAG AAGAAATATC     900

AACCAGATTA AGCATACAT CAGCATGCAT TCATACTCCC AGCATATAGT GTTTCCATAT     960

TCCTATACAC GAAGTAAAAG CAAAGACCAT GAGGAACTGT CTCTAGTAGC CAGTGAAGCA    1020

GTTCGTGCTA TTGAGAAAAC TAGTAAAAAT ACCAGGTATA CACATGGCCA TGGCTCAGAA    1080

ACCTTATACC TAGCTCCTGG AGGTGGGGAC GATTGGATCT ATGATTTGGG CATCAAATAT    1140

TCGTTTACAA TTGAACTTCG AGATACGGGC ACATACGGAT TCTTGCTGCC GGAGCGTTAC    1200

ATCAAACCCA CCTGTAGAGA AGCTTTTGCC GCTGTCTCTA AAATAGCTTG GCATGTCATT    1260

AGGAATGTTT AA                                                        1272

(2) INFORMATION FOR SEQ ID NO:2:

(i) SEQUENCE CHARACTERISTICS:
            (A) LENGTH: 423 amino acids
            (B) TYPE: amino acid
            (C) STRANDEDNESS:
            (D) TOPOLOGY: linear (ii) MOLECULE TYPE: protein (vi) ORIGINAL SOURCE:
            (F) TISSUE TYPE: Plasma (ix) FEATURE:
            (A) NAME/KEY: Peptide -continued (B) LOCATION: 23..401

(xi) SEQUENCE DESCRIPTION: SEQ ID NO:2:

```
Met Lys Leu Cys Ser Leu Ala Val Leu Val Pro Ile Val Leu Phe Cys
1               5                   10                  15

Glu Gln His Val Phe Ala Phe Gln Ser Gly Gln Val Leu Ala Ala Leu
            20                  25                  30

Pro Arg Thr Ser Arg Gln Val Gln Val Leu Gln Asn Leu Thr Thr Thr
        35                  40                  45

Tyr Glu Ile Val Leu Trp Gln Pro Val Thr Ala Asp Leu Ile Val Lys
50                  55                  60

Lys Lys Gln Val His Phe Phe Val Asn Ala Ser Asp Val Asp Asn Val
65                  70                  75                  80

Lys Ala His Leu Asn Val Ser Gly Ile Pro Cys Ser Val Leu Leu Ala
                85                  90                  95

Asp Val Glu Asp Leu Ile Gln Gln Ile Ser Asn Asp Thr Val Ser
            100                 105                 110

Pro Arg Ala Ser Ala Ser Tyr Tyr Glu Gln Tyr His Ser Leu Asn Glu
            115                 120                 125

Ile Tyr Ser Trp Ile Glu Phe Ile Thr Glu Arg His Pro Asp Met Leu
130                 135                 140

Thr Lys Ile His Ile Gly Ser Ser Phe Glu Lys Tyr Pro Leu Tyr Val
145                 150                 155                 160

Leu Lys Val Ser Gly Lys Glu Gln Thr Ala Lys Asn Ala Ile Trp Ile
                165                 170                 175

Asp Cys Gly Ile His Ala Arg Glu Trp Ile Ser Pro Ala Phe Cys Leu
            180                 185                 190

Trp Phe Ile Gly His Ile Thr Gln Phe Tyr Gly Ile Ile Gly Gln Tyr
        195                 200                 205

Thr Asn Leu Leu Arg Leu Val Asp Phe Tyr Val Met Pro Val Val Asn
210                 215                 220

Val Asp Gly Tyr Asp Tyr Ser Trp Lys Lys Asn Arg Met Trp Arg Lys
225                 230                 235                 240

Asn Arg Ser Phe Tyr Ala Asn Asn His Cys Ile Gly Thr Asp Leu Asn
                245                 250                 255

Arg Asn Phe Ala Ser Lys His Trp Cys Glu Glu Gly Ala Ser Ser Ser
            260                 265                 270

Ser Cys Ser Glu Thr Tyr Cys Gly Leu Tyr Pro Glu Ser Glu Pro Glu
        275                 280                 285

Val Lys Ala Val Ala Ser Phe Leu Arg Arg Asn Ile Asn Gln Ile Lys
290                 295                 300

Ala Tyr Ile Ser Met His Ser Tyr Ser Gln His Ile Val Phe Pro Tyr
305                 310                 315                 320

Ser Tyr Thr Arg Ser Lys Ser Lys Asp His Glu Glu Leu Ser Leu Val
                325                 330                 335

Ala Ser Glu Ala Val Arg Ala Ile Glu Lys Thr Ser Lys Asn Thr Arg
            340                 345                 350

Tyr Thr His Gly His Gly Ser Glu Thr Leu Tyr Leu Ala Pro Gly Gly
        355                 360                 365

Gly Asp Asp Trp Ile Tyr Asp Leu Gly Ile Lys Tyr Ser Phe Thr Ile
370                 375                 380

Glu Leu Arg Asp Thr Gly Thr Tyr Gly Phe Leu Leu Pro Glu Arg Tyr
385                 390                 395                 400

Ile Lys Pro Thr Cys Arg Glu Ala Phe Ala Ala Val Ser Lys Ile Ala
```

```
                    405               410               415
Trp His Val Ile Arg Asn Val
            420
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:3:

ATGGCCTATG AACCACAAG                                   19

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:4:

GTTTCTGGAA AAGAACAA                                    18

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:5:

AAAGAACAAG CAGCCAAAA                                   19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(xi) SEQUENCE DESCRIPTION: SEQ ID NO:6:

AAAGAACAAA CAGCCAAAA                                   19